United States Patent
Angeley

(10) Patent No.: US 6,451,010 B1
(45) Date of Patent: *Sep. 17, 2002

(54) ZOOM HANDPIECE FOR LASER SURGERY

(75) Inventor: David Angeley, San Jose, CA (US)

(73) Assignee: Lumenis Inc., Norwood, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/550,096

(22) Filed: Apr. 14, 2000

(51) Int. Cl.$^7$ ............................................. A61B 18/22
(52) U.S. Cl. ............................ 606/17; 606/2; 606/13; 606/10
(58) Field of Search .................................. 606/1–20

(56) References Cited

U.S. PATENT DOCUMENTS

| | | | |
|---|---|---|---|
| 4,601,037 A | | 7/1986 | McDonald |
| 5,336,216 A | | 8/1994 | Dewey .......................... 606/4 |
| 5,364,390 A | * | 11/1994 | Taboada et al. ............. 433/215 |
| 5,397,327 A | * | 3/1995 | Koop et al. .................... 606/17 |
| 5,558,666 A | | 9/1996 | Dewey et al. ................. 606/9 |
| 5,586,981 A | * | 12/1996 | Hu ................................ 606/9 |
| 5,743,902 A | | 4/1998 | Trost ........................... 606/18 |
| 5,783,798 A | * | 7/1998 | Abraham ............... 219/121.73 |
| 5,836,939 A | | 11/1998 | Negus et al. |
| 5,860,967 A | * | 1/1999 | Zavislan et al. ............... 606/10 |
| 5,957,915 A | * | 9/1999 | Trost ............................ 606/11 |
| 6,190,376 B1 | * | 2/2001 | Asah et al. .................... 606/11 |

OTHER PUBLICATIONS

R. Herloski, S. Marshall & R. Antos, "Gaussian beam ray–equivalent modeling and optical design," *Applied Optics*, vol. 22, No. 8, Apr. 15, 1983, pp. 11681174.
*Modern Optical Engineering*, "The Design of Optical Systems," subchaper 9.10, by Warren J. Smith, 2nd Edition, Copyright 1990 by McGraw–Hill, Inc., pp. 273–278.
R. Herloski, S. Marshall & R. Antos, "Gaussian beam ray–equivalent modeling and optical design," *Applied Optics*, vol. 22, No. 8, Apr. 15, 1983, pp. 11681174.
*Modern Optical Engineering*, "The Design of Optical Systems," subchapter 9.10, by Warren J. Smith, 2nd Edition, Copyright 1990 by McGraw–Hill, Inc., pp. 273–278.

* cited by examiner

Primary Examiner—Lee Cohen
Assistant Examiner—Hank M. Johnson
(74) Attorney, Agent, or Firm—Eitan, Pearl, Latzer & Cohen-Zedek

(57) ABSTRACT

A handpiece for projecting laser radiation from a solid-state laser via an articulated arm to biological tissue being treated is disclosed. An optical system in the handpiece provides that the laser radiation is projected in a spot of selectively variable size at a fixed distance from the handpiece. The projected spot can be defined as an image of a characteristic invariant cross-section of the laser beam delivered to the handpiece which has about the same width at a wide range of $M^2$ values of the laser beam. This provides that at any mechanically selected size, the size of the projected spot remains substantially constant over the range of $M^2$ values between about 1 and 15. In one example the handpiece projects 2.94 $\mu$m radiation in a range of spot sizes between about 0.5 mm and 1.5 mm. Spot size remains substantially constant over a range of $M^2$ values between about 1 and 15.

16 Claims, 6 Drawing Sheets

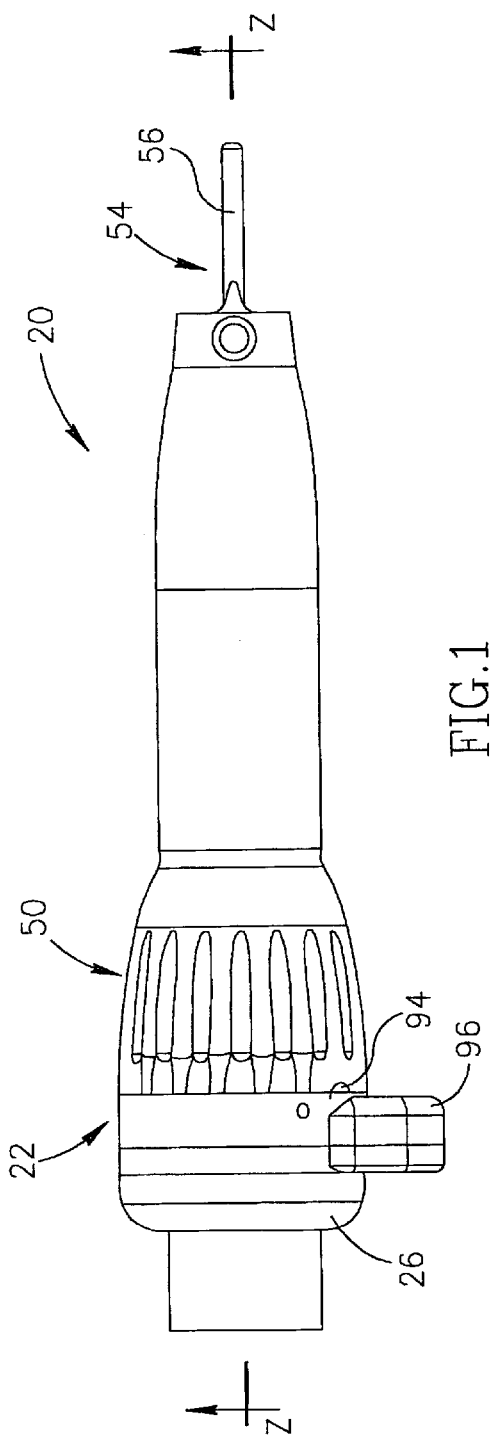
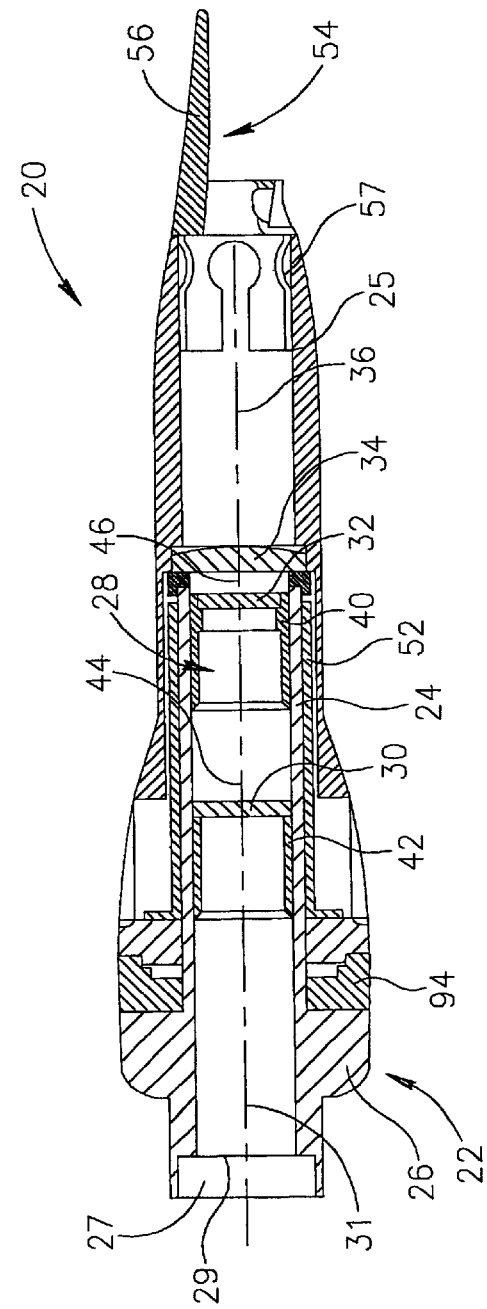
FIG.1
FIG.2

ZOOM HANDPIECE FOR LASER SURGERY

TECHNICAL FIELD OF THE INVENTION

The present invention relates in general to handpieces for delivering laser radiation from a solid-state laser to biological tissue for the purpose of making a surgical incision therein. The invention relates in particular to a handpiece which is operable to provide a selectively variable spot size of laser radiation at an incision site at a fixed distance from the handpiece.

DISCUSSION OF BACKGROUND ART

Laser radiation is used in surgical procedures to make incisions in soft or hard biological tissue. The radiation is generated by a laser apparatus and transported from the laser apparatus to a surgical site by an optical fiber or an articulated arm. Delivery by articulated arm is a preferred method in particular for efficiently transmitting infrared wavelengths such as the 2.94 micrometer ($\mu$m) wavelength of the (solid-state) Er:YAG laser. An optical system is typically incorporated in a handpiece attached to the arm for focussing the beam to a spot of a size required for the incision.

The use of laser radiation to make an incision offers an advantage over a conventional surgical incision instrument such as a scalpel or the like in that it can reduce bleeding as a result of the incision because of an attendant cauterization effect. Laser radiation also offers a high degree of flexibility in the kind of incisions that can be made. By way of example, an elongated incision can be made by operating a handpiece to move a fine focussed spot of radiation over tissue in the direction in which the elongated incision is desired. Alternatively, the handpiece can be held steady and the spot delivered thereby held in one position to "drill" a hole in hard tissue or bone. Ability to vary the spot size could provide for an ability to vary the diameter of holes being drilled.

Flexibility and convenience of laser surgical incision would be improved were a handpiece available which could provide a range of beam spot sizes from a beam delivered by a single laser apparatus. A particular problem in providing such a handpiece, however, is that variation of the spot size can require a corresponding variation in laser output power to maintain a constant fluence at the point of incision. In solid-state lasers, variation of the output power typically results in a variation in output beam diameter and divergence (beam quality). There is a need for a handpiece that will not only provide an incision spot of variable spot size but will maintain a selected spot size for a wide range of beam quality in a laser beam delivered to the handpiece.

SUMMARY OF THE INVENTION

The present invention is directed to a handpiece for receiving a beam of laser radiation from an optically-pumped solid-state laser via an articulated arm and projecting the radiation onto biological tissue for making an incision therein. The laser beam has a beam quality defined by a value $M^2$ which varies according to the power of optical pumping.

In one aspect, the inventive handpiece comprises an arrangement at a proximal end thereof for attaching the handpiece to the articulated arm for receiving the laser radiation therefrom. An optical system is provided within the handpiece for projecting the received radiation. A probe is provided at a distal end of the handpiece for contacting the tissue being treated. The probe establishes a fixed working distance between the optical system and tissue being treated. The optical system is adjustable for selectively varying the size of a spot of laser radiation projected thereby on the tissue at the fixed working distance from a minimum value to a maximum value, and is arranged such that the size of any selected spot is about the same at any value of $M^2$ between about 1.0 and 15.0.

In another aspect of the inventive handpiece the laser beam has a location therein at which the beam cross-section is about the same at all values of $M^2$. The optical system is arranged to project an image of the invariant cross-section of the laser beam at a fixed distance from the optical system. The projected spot corresponds to the projected image. The effective focal of the optical system is variable for selectively varying the size of the projected spot.

In one preferred embodiment the optical system comprises three optical elements. The fixed distance is measured from a fixed one of the optical elements to the end of the probe, i.e., to the incision site. The other two optical elements are moveable with respect to the fixed optical element for varying the spot size.

The inventive optical system is particularly useful for delivering laser-radiation from an erbium-doped YAG (Er:YAG) laser. Er:YAG has a particularly high thermal lensing coefficient (about 80 diopters per meter per Kilowatt) compared with other solid-state gain media. Accordingly, variations in pump power made to vary output power can lead to substantial variations in $M^2$. The inventive handpiece is able to accommodate such variations while still maintaining a projected spot size at about its selected width.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

FIG. 1 is an elevation view schematically illustrating an exterior arrangement of a preferred embodiment of a handpiece in accordance with the present invention.

FIG. 2 is a longitudinal cross-section view of the handpiece of FIG. 1 seen generally in a direction 2—2 of FIG. 1 and illustrating details of an optical system in accordance with the present invention and a mechanism for moving elements of the optical system with respect to each other.

DETAILED DESCRIPTION OF THE INVENTION

Figure 3:
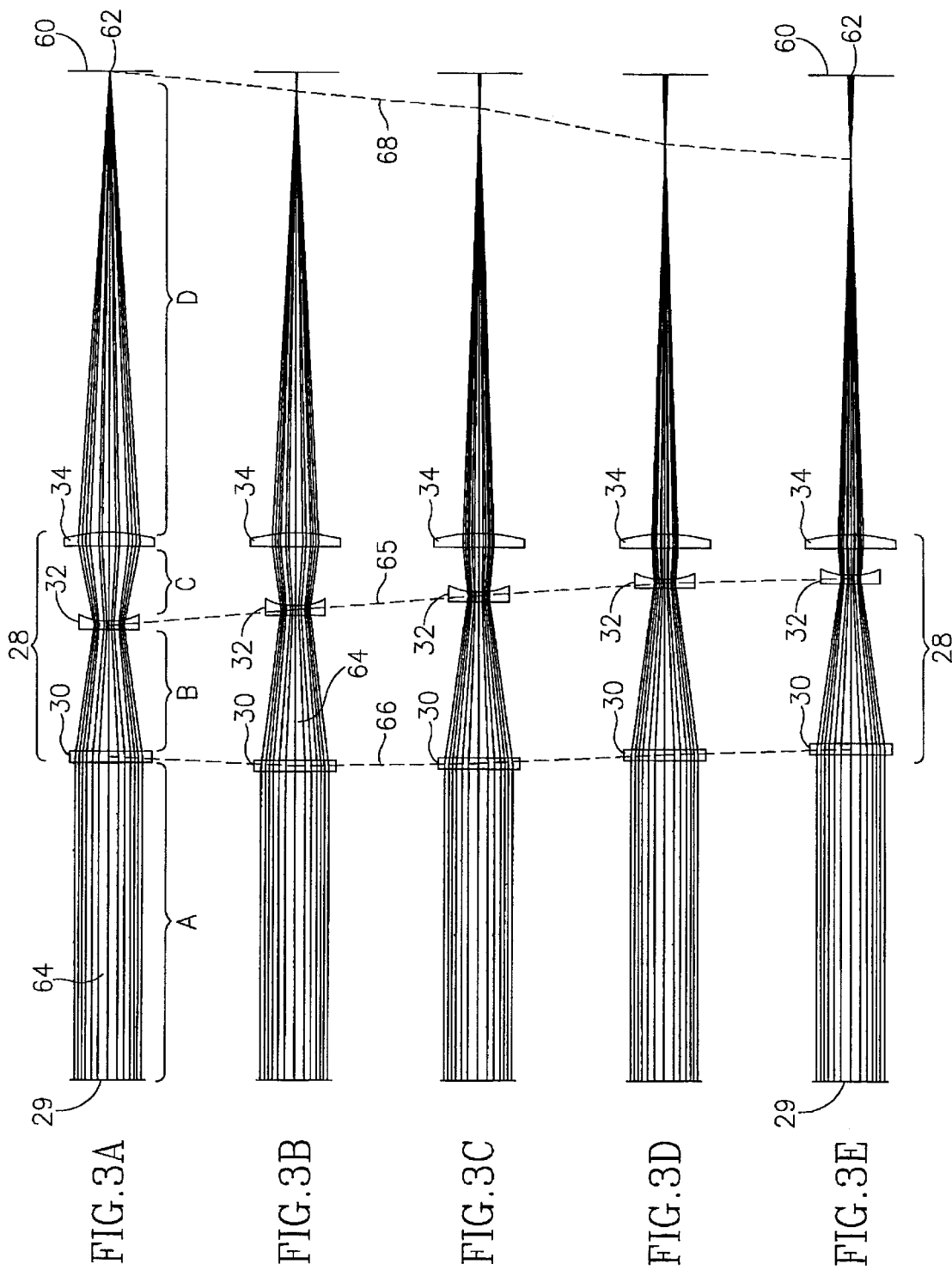
FIGS. 3A–E are paraxial ray traces schematically illustrating various relative spacings of optical elements of the optical system of FIG. 2 for providing different spot sizes at a fixed distance from the optical system.

Turning now to the drawings, wherein like features are illustrated by like reference numerals, FIG. 1 and FIG. 2 schematically depict, respectively, external features and internal details of a handpiece 20 in accordance with the present invention. Handpiece 20 includes a hollow cylindrical chassis 22 having an elongated cylindrical portion 24 extending from a head portion 26 of larger diameter. Head portion 26 includes a socket 27 for attaching the handpiece to a laser radiation delivery arm or articulated arm (not shown).

Mounted within portion 24 of chassis 22 is a variable-focus ("zoom") optical system 28 including optical elements 30, 32 and 34. Optical system 28 has a longitudinal axis 31 collinear with the longitudinal axis of chassis 22. The base of socket 27 defines a plane 29 which denotes the end of the articulated arm and the beginning of optical system 28. Element 34 of the optical system is fixedly held in chassis 22. Elements 30 and 32 of the optical system are mounted on carriers 42 and 40 respectively. Carriers 40 and 42 are slidably mounted within portion 24 of chassis 22. Pins 44 and 46, attached to carriers 42 and 40 respectively, extend through an axially-extending slot (not shown) in chassis 22. This essentially prevents rotation of the carriers in chassis 22.

Mounted on portion 24 of chassis 22 is a rotatable adjustment or spot-size selection knob 50. Knob 50 is attached to a cam-sleeve 52 rotatably fitting over portion 24 of chassis 22. Pins 44 and 46 each extend through a (separate) cam slot (not shown) in cam-sleeve 52. The cam slots are arranged generally transverse to longitudinal axis 31 and are curved such that rotary motion of adjustment knob 50 varies the axial position of carriers 40 and 42, and, accordingly, optical elements 32 and 30 thereon. Varying the axial position of the optical elements varies the spot size of a laser beam projected by optical system 28 at a fixed distance from handpiece 20. Optical system 28 and the cam arrangements for varying the relative position of optical elements thereof are discussed in detail further hereinbelow.

A standoff tip 54 includes a probe portion 56. During operation of handpiece 20, the standoff tip is attached to a standoff sleeve 25 attached to chassis 22. A distal end of probe portion 56 of standoff tip 54 is held in contact with tissue in which an incision is being made. This provides that the distance between optical system 28 and the tissue being treated is the distance from the tissue at which the optical system is designed to operate. Standoff tip 54 is removably attached (plugged into) to sleeve 25 via a cylinder-spring member 57 of the standoff tip. This allows removal of the tip for sterilization.

Referring now to FIGS. 3A, 3B, 3C, 3D, and 3E, in one preferred arrangement of variable focus optical system 28 there are three variable element-spacings A, B and C, and a fixed element-spacing D. Spacing A is the spacing between plane 29 of socket 27 (the delivery end of handpiece 20) and element 30. Spacing B is the spacing between element 30 and element 32. Spacing C is the spacing between element 32 and element 34. Fixed spacing D is the spacing between tissue 60 and fixed element 34 and is established as discussed above by standoff-tip 54 of handpiece 20. Laser radiation is deposited in a spot 62 on the tissue, determined by the beam width at that point. In the example of FIGS. 3A–E, elements 30 and 34 have positive optical (dioptric) power, and element 32 has negative dioptric power.

FIGS. 3A, 3B, 3C, 3D, and 3E represent geometrical ray traces through optical system 28 from an object at about 1500 mm in front of element 30. The input beam diameter has been increased beyond the design beam diameter to illustrate tolerance to misalignment. FIG. 3A shows the spacing arrangement for the smallest diameter of spot 62, with spot 62, here, being located at about the paraxial focus system 28. In FIG. 3A, optical system 28 has its longest back focal length (the distance of the paraxial focus from element 34). The size of spot 62 is progressively increased primarily by progressively moving element 32 toward element 34 as illustrated by dotted line 65. There is a corresponding, albeit relatively smaller, motion of element 30, indicated by dotted line 66.

In response to the indicated change in relative spacing of elements 30, 32, and 34, the effective focal length of optical system 28 increases and the paraxial focus of optical system 28 moves away from tissue surface 62, toward the optical system, generally as indicated by dotted line 68. The distance from element 34 to the paraxial focus, as noted above, is the back focal length or back focal distance of optical system 28.

It should be noted, here, that the geometrical ray traces of FIG. 3 are presented primarily to illustrate design of the inventive optical system in geometrical optics terms for the purpose of defining a preferred variable focus or zoom arrangement. As discussed hereinbelow, however, in the application contemplated for the inventive handpiece, principles of the inventive spot size formation and variation can not easily be derived from such simple ray trace considerations. The spot must be formed from an input beam having a Gaussian energy distribution and a diameter and divergence which vary according to power in the beam. Optical system 28 is designed to accommodate an input beam having a variable diameter and divergence corresponding to a value of $M^2$ varying between 1.0 and about 15.0, where $M^2$ can be defined as the ratio of the actual to ideal (diffraction limited) Gaussian beam quality, as is known in the art. This variation can be expected in a solid-state laser apparatus as pump power is varied to vary output power. The variation in results, inter alia, from a variation in thermal lensing in the solid-state gain medium of the laser with variation in pump power supplied thereto.

Figure 5:
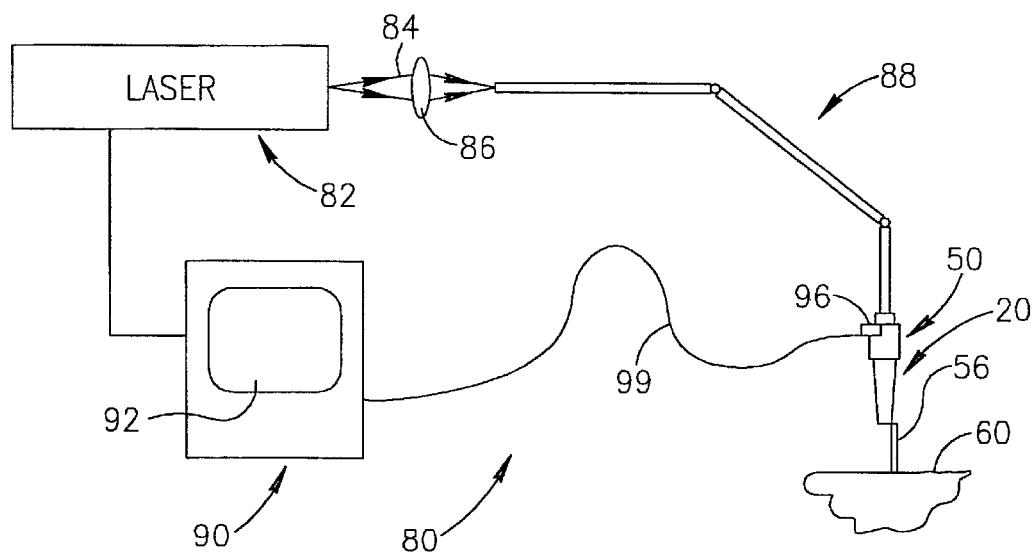

Design principles of the inventive handpiece were evolved by considering the imaging properties of optical system 28 in a Gaussian beam propagation therethrough in conjunction with the behavior of a Gaussian beam delivered by a solid-state laser resonator under different thermal lensing conditions. A laser system delivering the radiation is schematically depicted in FIG. 5. Here a laser system 80 includes such a laser 82, delivering laser radiation 84. Laser radiation 84 is focused by telescope optics 86 into an articulated arm 88, which delivers the radiation to handpiece 20. Laser 82 is controlled by a controller 90 including a touch-screen display 92 for setting and displaying operating parameters of the system. Handpiece 20 (see FIGS. 1 and 2) includes electronic circuitry (not individually shown), assembled on a printed circuit board (PCB) 94 (see FIG. 8). The circuitry is cooperative with spot-size adjustment (spot-size selection) knob 50 and provides an electronic representation of the selected spot size. A connector 96 enables electronic connection with PCB 94 for reading the spot-size representation. Details of the circuitry are discussed further herein below.

Figure 6:
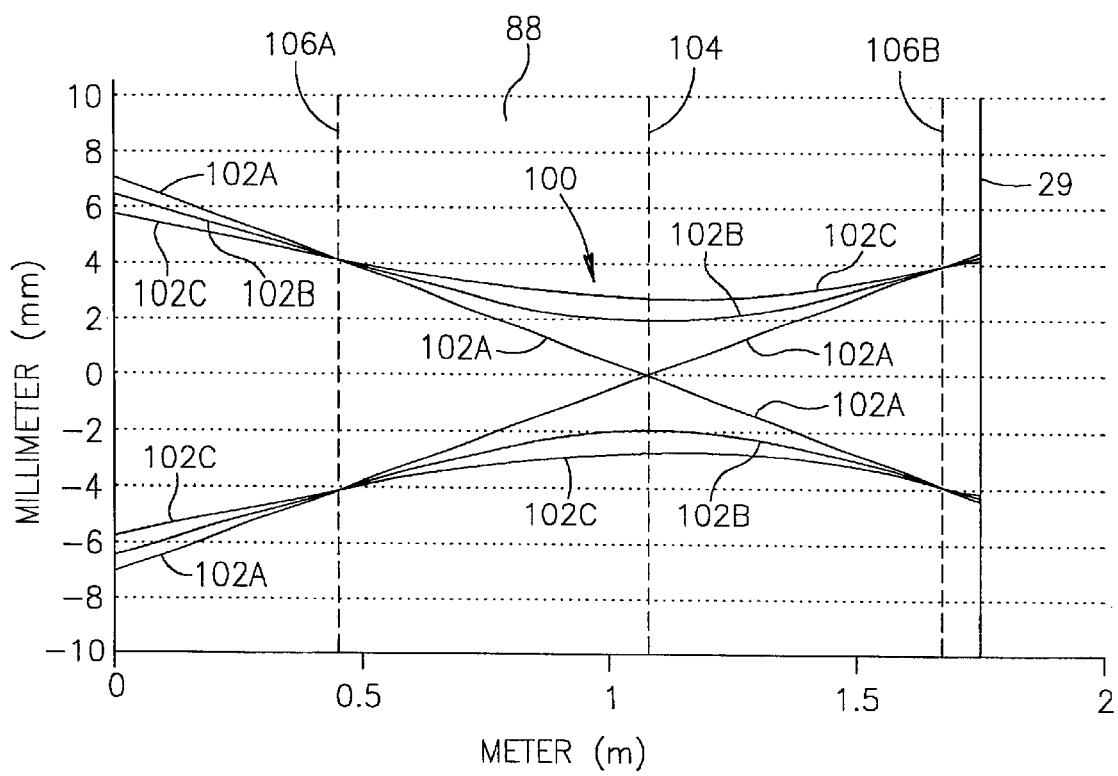
FIG. 6 schematically illustrates a waist portion of a Gaussian laser beam delivered by the laser of FIG. 5 propagating in the articulated arm of FIG. 5.

FIG. 6 schematically illustrates the shape of a Gaussian beam 100 within articulated arm 88. The beam shape, here, is an image of the beam in the vicinity of a plane-output coupling mirror of a plano-plano (flat-flat) laser resonator having an approximately centrally located solid-state gain-medium (not shown) exhibiting positive thermal lensing under normal operating conditions.

Curves 102A, show the computed form of the beam when thermal lensing is at a minimum (lowest pumping power for the gain-medium), providing a value of $M^2$ of about 1.07. Curves 102B and 102C show the form of the beam at increasingly higher values of $M^2$ (11.08 and 13.33 respectively) resulting from higher pumping power and greater thermal lensing. In this example the $M^2$ values result from thermal lensing in the gain-medium of about 59.0, 110.0 and 170.0 diopters per meter (dpm) respectively.

It can be seen that at any value of thermal lensing there is a narrowest region (waist) of the beam designated by dashed line 104. Line 104 corresponds approximately to an image (formed by telescope optics 86) of the surface of the laser output coupling mirror. The waist becomes increasingly wider and the beam divergence decreases with increasing $M^2$. There are, however, locations on either side of the beam waist (designated by dashed lines 106A and 106B) where the beam width is essentially invariant with thermal lensing or $M^2$. Optical system 28 is designed to form a real "image" of invariant location 106A at about the working distance D from the optical system. This image provides the laser spot size for the incision. As the spot is essentially a real image of the invariant portion of the laser beam, its size (at any setting within the design range of optical system 28) can be expected not to vary significantly with the variations in thermal lensing or $M^2$.

Figure 7A:
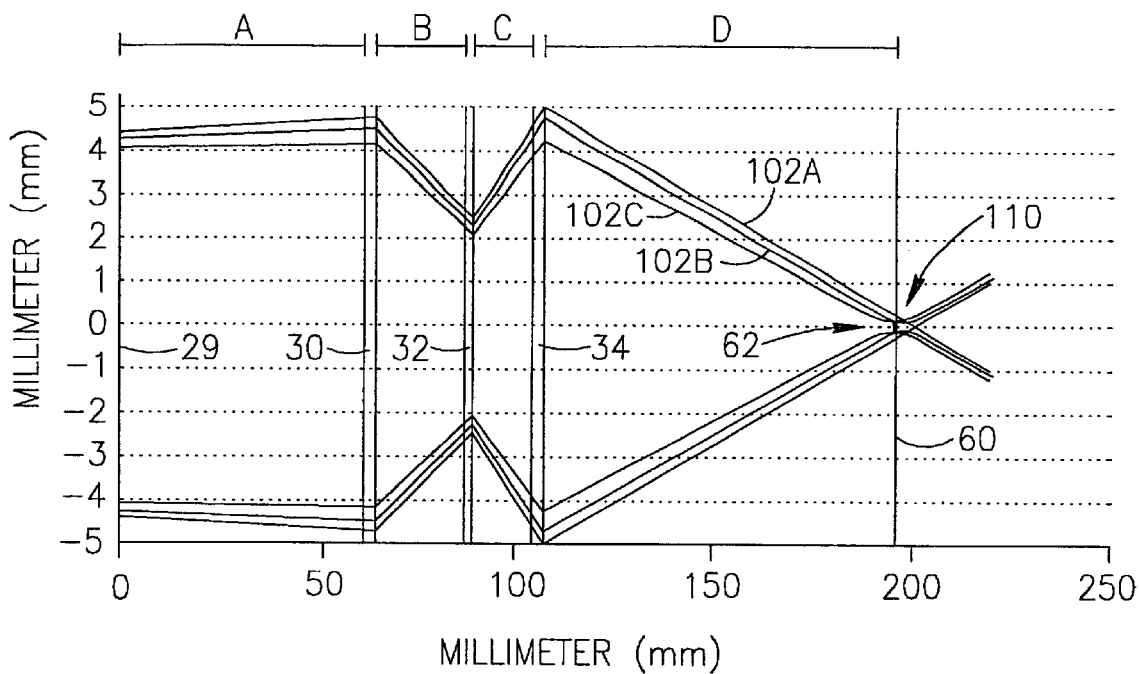
FIGS. 7A–C schematically illustrate the form of the Gaussian laser beam of FIG. 6 propagating through the optical system arrangements of FIGS. 3A, 3C and 3E respectively.
Figure 7B:
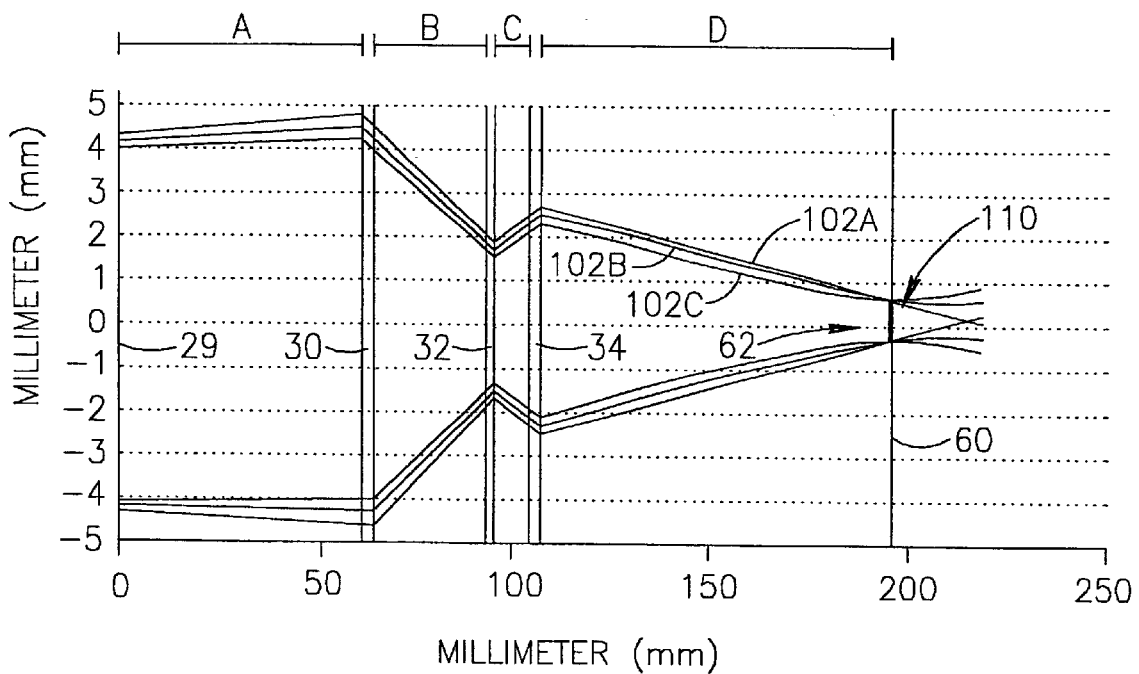
Figure 7C:
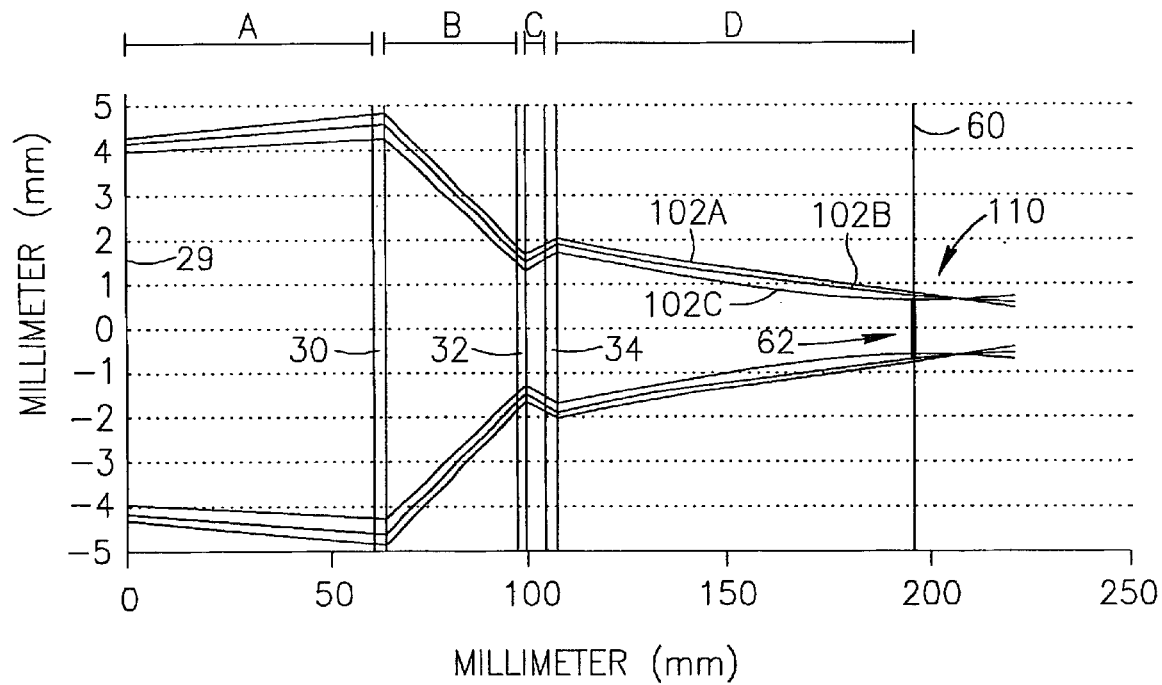

FIGS. 7A, 7B, and 7C show the form of the Gaussian beam delivered by articulated arm 88 as it traverses optical system 28 and passes through a plane 60 representative of tissue at working distance D of FIGS. 3A–E. FIGS. 7A–C represent settings of optical system 28 corresponding to the configurations of FIGS. 3A, 3C, and 3E, i.e., for respectively the smallest, a middle and the largest contemplated spot size. Curved surfaces of optical elements 30, 32, and 34, are represented in FIGS. 7A–C as planes, as is usual in such a Gaussian beam paraxial analysis. In each case, there are curves 102A–C representing the three thermal lensing (or $M^2$) conditions of FIG. 6.

In FIG. 7A, working distance D sets plane 60 about coincident with the image 110 of the invariant region 106A of the beam. In each case, the intersection of plane 60 with the beam defines the spot size. Beams are shown progressing beyond plane 60 to assist in understanding principles of the invention. In practice, with tissue at plane 60 absorption of radiation in the tissue would prevent further propagation. In FIGS. 7B and C, the invariant location is respectively slightly ahead (about 5 mm) and slightly behind (about 5 mm) plane 60. In these cases, however, the Rayleigh range of the beam is sufficiently long that the slight mismatch of the invariant position with the working distance provides that the spot sizes can still remain about constant, for example within about ±10% of nominal. Interestingly, while there is only a relatively small variation in the invariant image position through the spot size range, the waist image position varies from less than 10.0 mm behind plane 60 for the smallest spot size to about 60.0 mm for the largest spot size. This waist image shift more or less tracks an image shift which would be predicted by geometrical optics considerations.

In one preferred example of an optical system in accordance with the layout of FIGS 3A–E, element 30 is a plano-convex element having an effective focal length of 50.0 mm, an axial thickness of 2.31 mm and a clear aperture of 13.5 mm. Element 32 is a plano-concave element having an effective focal length of −10.0 mm, an axial thickness of 1.7 mm and a clear aperture of 8 mm. Element 34 is a plano-convex element having an effective focal length of 25.0 mm, an axial thickness of 3.0 mm and a clear aperture of 17.3 mm. Elements 30, 32, and 34 are all made from zinc selenide.

The system is designed in general to accept a laser beam having a wavelength of about 2.94 μm, having an $M^2$ between 1.0 and about 15, and having a diameter of about 8.5 mm at plane 29 of handpiece 20, with the beam waist in articulated arm 88 located at about 664.0 mm from plane 29. The system provides for minimum and maximum spot sizes of about 0.5 mm and 1.50 mm respectively at a theoretical optimum working distance D of about 88.8±1.0 mm. Beam spot size, here, is defined as the knife-edge displacement between the 10% and 90% power points multiplied by a 1.561 scale factor. Values for spacings A, B, and C for various spot sizes within the design range are listed in TABLE 1.

Figure 4:
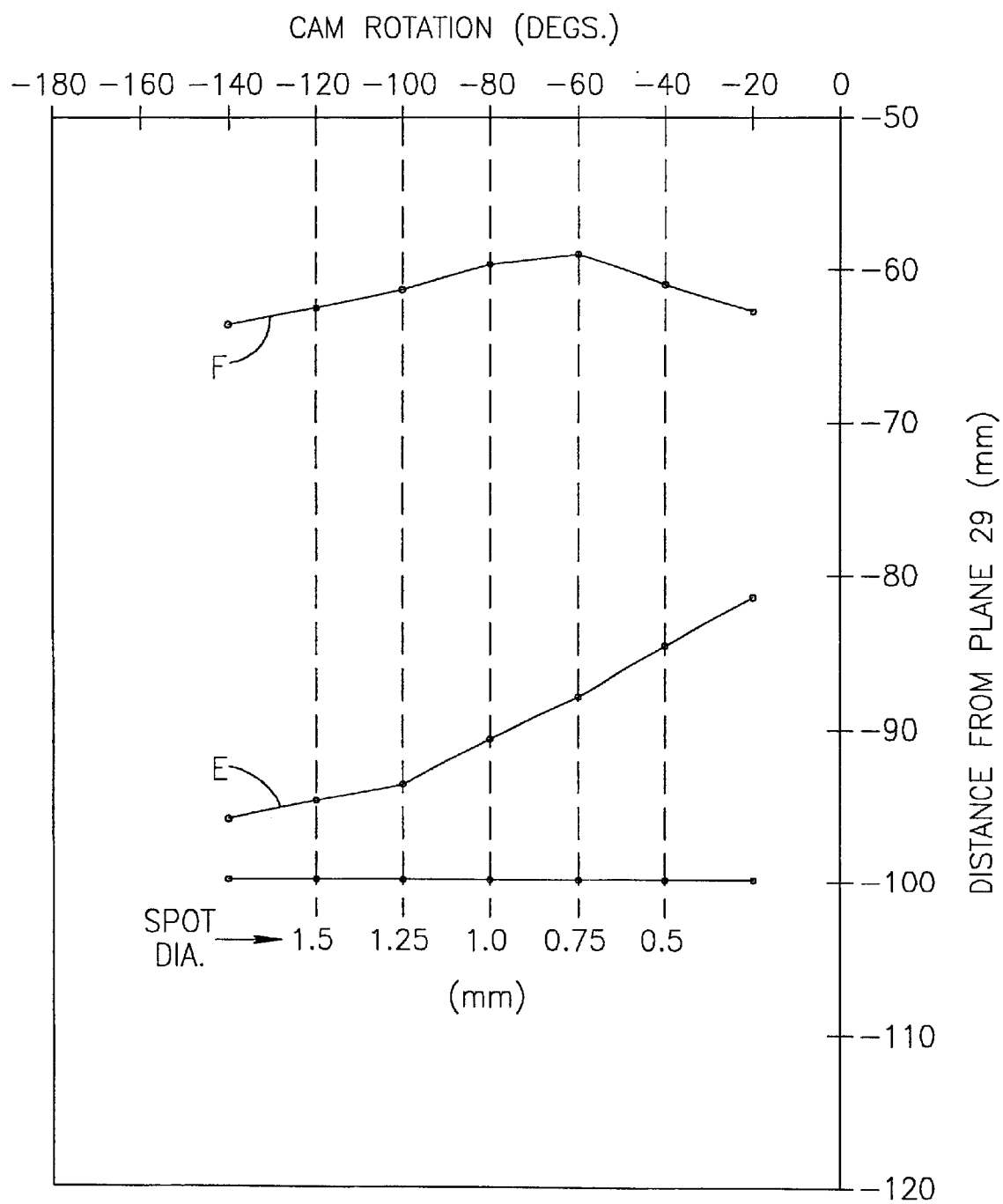
FIG. 4 is a graph schematically illustrating the form of cams in the mechanism for moving optical elements of FIG. 2 FIG. 5 schematically illustrates the handpiece of FIG. 1 receiving laser radiation from a laser via an articulated arm, and an electronic connection between the handpiece and a controller controlling the laser for controlling energy of laser radiation delivered by the laser.

The cam angle in TABLE 1 refers to the degree of rotation of cam-sleeve 52 (see FIG. 2). The shape of cam slots in sleeve 52 are schematically depicted graphically in FIG. 4. Here, curves E and F show the shape of cam slots for moving elements 32 and 30 respectively. The shape of the slots is depicted in the form they would take if cam-sleeve 52 were "unrolled" from its cylindrical form.

TABLE 1

| Spot Size (mm) | A (mm) | B (mm) | C (mm) | Cam Angle (Degrees) | Effective Focal Length (mm) |
|---|---|---|---|---|---|
| 0.50 | 61.00 | 23.50 | 15.50 | 40 | 88 |
| 0.75 | 59.10 | 28.50 | 12.40 | 60 | 123 |
| 1.00 | 59.70 | 31.10 | 9.20 | 80 | 149 |
| 1.25 | 61.30 | 32.50 | 6.20 | 100 | 165 |
| 1.50 | 62.60 | 32.40 | 5.00 | 120 | 180 |

It can be seen from Table 1 that the spot size does not change linearly with the effective focal length of optical system 28 as might be expected from a simple geometrical optics consideration of such an optical system design. A relative change in effective focal length of about 2.05 produces a factor of 3.0 increase in spot size. This at least serves to illustrate that while design of such an optical system may begin from geometrical optics considerations, it is important in arriving at a final design to follow the Gaussian analysis approach as described above.

It should be noted here that, in practice, there may occur some relatively small variation of the invariant image locations from those predicted by a paraxial Gaussian analysis. This could occur, inter alia, due to variations in the beam from a true Gaussian, aberrations, as well as due to normal manufacturing tolerances. By way of example, a theoretically optimal working distance for the system of table one is about 89.0 mm. The final refinement to the practical optimum of 92 mm was simply effected, experimentally, by adjustment of the length of stand-off probe 56.

Continuing now with a description of electronic aspects of the inventive handpiece, laser radiation fluence (energy per unit area) delivered by handpiece 20 to tissue at the working distance D depends on the selected spot size, i.e., the area of the spot and the energy delivered to the handpiece via the articulated arm from a laser. If energy delivered by the laser is constant, then changing the spot size will change the fluence at the tissue. As discussed above, handpiece 20 includes an electronic arrangement for indicating the spot size that has been selected by adjustment knob 50.

Referring again to FIG. 5, in system 80, controller 90 monitors spot-size data from PCB 94 (See FIG. 8) via a cable 99 connected to connector 96. The spot-size data is used by the controller to determine laser output energy required to provide an operator-selected fluence. This provides that the selected fluence remains constant independent of the selected spot size. Such a feature is not only convenient for an operator of system 80 (and handpiece 20) but provides a safety measure, inasmuch as inadvertent operation of knob 50 resulting in a smaller spot size will not result in a correspondingly increased fluence.

Figure 8:
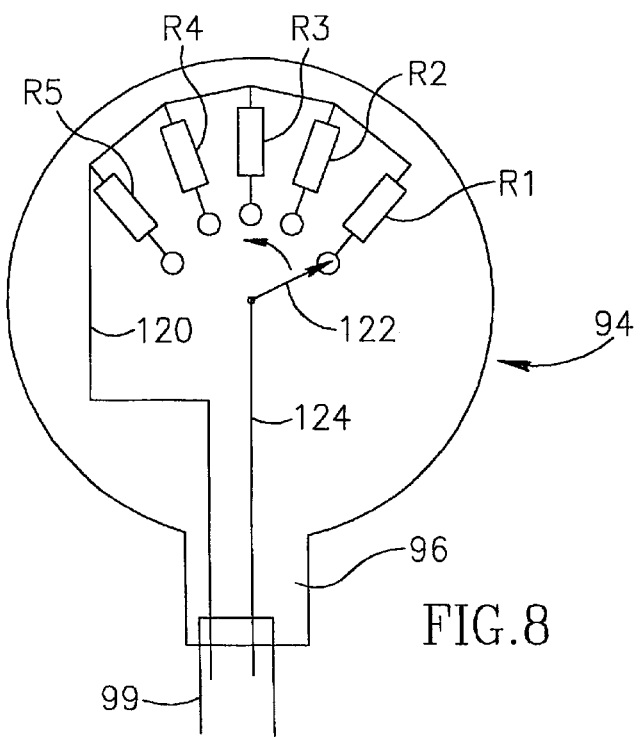
FIG. 8 schematically illustrates an electronic arrangement for indicating a selected spot size of the handpiece of FIGS. 1 and 2 to the controller of FIG. 5.

FIG. 8 schematically depicts one preferred arrangement of electronics in PCB 94 for indicating a selected spot size. Here resistors R1, R2, R3, R4 and R5 each have a different value representative of one of a range of selectable spot sizes. Each of the resistors has one side thereof connected to a lead 120 connectable in connector 96 with cable 99. The opposite side of any of the resistors can be connected to cable 99 by a rotatable contact or "wiper" 122 and a lead 124. Wiper 122 is operated by rotation of adjustment knob 50 for selecting a particular spot size.

In summary, a novel handpiece for projecting laser radiation from a solid-state laser via an articulated arm to tissue being treated is described above. An optical system in the handpiece provides that the laser radiation is projected in a spot of selectively variable size at a fixed distance from the handpiece, The spot can be defined as an image of a characteristic invariant cross section of the laser beam delivered to the handpiece which has about the same width at a range of $M^2$ values of the laser beam. This provides that at any selected size, the size of the spot remains substantially constant over a range of $M^2$ between about 1 and 15.

The present invention is described above in terms of a preferred and other embodiments. The invention, however, is not limited to the apparatus described and depicted. Rather the invention is limited only by the claims appended hereto.

What is claimed is:

1. A handpiece for receiving a beam of laser radiation from a solid-state laser via an articulated arm and projecting the radiation onto biological tissue for making an incision therein, the laser beam having a beam quality defined by a value $M^2$, the handpiece comprising:

an arrangement at a proximal end of the handpiece for attaching the handpiece to the articulated arm for receiving the laser radiation therefrom;

an optical system within the handpiece for projecting the received radiation;

a probe at a distal end of the handpiece for contacting the tissue being treated, thereby establishing a fixed working distance between the optical system and tissue being treated; and said optical system being adjustable for selectively varying the size of a spot of laser radiation projected thereby on the tissue at said fixed working distance from a minimum value to a maximum value and arranged such that the size of any selected spot is about the same at any value of $M^2$ between about 1.0 and 15.0.

2. The handpiece of claim 1, wherein said minimum and maximum spot size values are respectively about 0.5 mm and 1.5 mm.

3. The handpiece of claim 2, wherein said laser radiation has a wavelength of about 2.94 micrometers.

4. The handpiece of claim 1, wherein said optical system includes first second and third optical elements numbered in consecutive numerical order in the direction of propagation of laser radiation therethrough, said first and third optical elements having positive dioptric power and said second optical element having negative dioptric power, said third optical element being held in a fixed position and at least said second optical element being movable with respect to said first optical element.

5. The handpiece of claim 4, wherein said first and second optical elements are movable with respect to said third optical element.

6. The handpiece of claim 4, wherein said fixed distance is measured from said third optical element to a distal end of said probe.

7. The handpiece of claim 4, wherein said optical elements are zinc selenide optical elements.

8. The handpiece of claim 4 further including an electronic arrangement cooperative with a mechanism for moving said optical elements and connectable to a controller of the solid-state laser for indicating the size of a selected spot.

9. A handpiece for receiving beam of laser radiation from an optically-pumped solid-state laser via an articulated arm and projecting the radiation onto biological tissue for making an incision therein, the laser beam having a beam quality defined by a value $M^2$ which varies with optical-pumping power, and having a location therein at which the beam cross-section is substantially invariant with respect to $M^2$, the handpiece comprising:

an optical system arranged to project an image of the invariant cross-section of the laser beam in a selectively variable spot size at a fixed distance from the optical system.

10. The handpiece of claim 9, wherein said optical system has a variable effective focal length and said image size is selectively varied by varying the focal length of said optical system.

11. A handpiece for receiving beam of laser radiation from an optically-pumped solid-state laser via an articulated arm and projecting the radiation onto biological tissue for making an incision therein, the laser beam having a beam quality defined by a value $M^2$ which varies with optical-pump power, and having at a location therein within the articulated arm a beam cross-section which is essentially invariant with respect to $M^2$, the handpiece comprising:

an arrangement at a proximal end of the handpiece for attaching the handpiece to the articulated arm for receiving the laser radiation therefrom;

an optical system within the handpiece for projecting the received radiation;

a probe at a distal end of the handpiece for contacting the tissue being treated, thereby establishing a fixed working distance between the optical system and tissue being treated;

said optical system arranged to project said received radiation into a spot at said fixed distance from the optical system, and arranged such that the size of said spot is selectively variable within a predetermined range; and wherein said spot corresponds to an image of the invariant cross-section of the laser beam, whereby said selected spot size is about the same at any value of $M^2$ between about 1.0 and 15.0.

12. The handpiece of claim 11, wherein optical system has a variable effective focal length and said spot size selection is effected by varying said effective focal length.

13. The handpiece of claim 12, wherein said optical system includes first second and third optical elements numbered in consecutive numerical order in the direction of propagation of laser radiation therethrough, said first and third optical elements having positive dioptric power and said second optical element having negative dioptric power, said third optical element being held in a fixed position and said first and second optical elements being movable with respect to said first optical element.

14. A handpiece for receiving a beam of laser radiation from a solid-state laser via an articulated arm and projecting the radiation onto biological tissue for making an incision therein, the laser beam having a beam quality defined by a value $M^2$, the handpiece comprising:

an arrangement at a proximal end of the handpiece for attaching the handpiece to the articulated arm for receiving the laser radiation therefrom;

an optical system within the handpiece for projecting the received radiation;

a probe at a distal end of the handpiece for contacting the tissue being treated, thereby establishing a fixed working distance between the optical system and tissue being treated;

said optical system being adjustable for selectively varying the size of a spot of laser radiation projected thereby on the tissue at said fixed working distance from a minimum value to a maximum value;

a mechanism for effecting said selective adjustment; and an electronic arrangement cooperative with a said mechanism and connectable to a controller of the solid-state laser for indicating the size of a selected spot.

15. The handpiece of claim 14, wherein said optical system is arranged such that the size of any selected spot is about the same at any value of $M^2$ between about 1.0 and 15.0.

16. A laser system for treating tissue comprising:

a laser for generating a treatment beam;

a controller for varying the pump power to the laser for varying the output power of the treatment beam; and an arrangement for delivering the treatment beam from the laser to the tissue to be treated, said arrangement including a handpiece having adjustable optical elements for varying the spot size of the beam reaching the tissue, said handpiece including circuitry for generating an output signal corresponding to the selected spot size, and wherein said controller receives said output signal from said handpiece and adjusts the pump power to the laser in response thereto to obtain a selected fluence level at the tissue.

* * * * *